(12) United States Patent
Lavigne

(10) Patent No.: US 6,543,452 B1
(45) Date of Patent: Apr. 8, 2003

(54) NASAL INTUBATION DEVICE AND SYSTEM FOR INTUBATION

(75) Inventor: Francois Lavigne, Ville Mont Royal (CA)

(73) Assignee: Medilyfe, Inc. (CA)

( * ) Notice: Subject to any disclaimer, the term of this patent is extended or adjusted under 35 U.S.C. 154(b) by 62 days.

(21) Appl. No.: 09/714,075

(22) Filed: Nov. 16, 2000

(51) Int. Cl.⁷ .............................................. A61M 15/08
(52) U.S. Cl. ........................... 128/207.18; 128/201.18; 128/206.29; 604/541; 604/94.01; 604/104; 606/127; 606/159; 606/198
(58) Field of Search ..................... 128/201.18, 207.18, 128/206.29, 911, 912; 604/541, 94.01, 104, 105, 106; 606/127, 159, 198, 200, 108, 167, 185

(56) References Cited

U.S. PATENT DOCUMENTS

| | | | |
|---|---|---|---|
| 858,996 A | | 7/1907 | Lamport |
| 2,099,127 A | | 11/1937 | Leech |
| 2,431,587 A | | 11/1947 | Schnee |
| 2,859,518 A | | 11/1958 | Cohn |
| 3,363,629 A | | 1/1968 | Kuhn |
| 3,540,431 A | * | 11/1970 | Mobin-Uddin ............. 128/899 |
| 3,599,642 A | | 8/1971 | Tindel |
| 3,815,600 A | * | 6/1974 | Groves ....................... 604/286 |
| 3,874,388 A | * | 4/1975 | King et al. .................. 606/232 |
| 3,894,539 A | * | 7/1975 | Tallent ........................ 604/215 |
| 3,964,488 A | | 6/1976 | Ring et al. |
| 4,007,743 A | * | 2/1977 | Blake ......................... 606/232 |
| 4,056,104 A | | 11/1977 | Jeffe |
| D258,531 S | | 3/1981 | Orsing |
| 4,389,208 A | * | 6/1983 | LeVeen et al. .............. 604/106 |
| 4,508,535 A | | 4/1985 | Joh et al. |
| 4,627,838 A | * | 12/1986 | Cross et al. ................. 604/105 |
| 4,643,716 A | | 2/1987 | Drach |
| 4,737,141 A | * | 4/1988 | Spits .......................... 604/106 |
| 4,863,430 A | * | 9/1989 | Klyce et al. ............ 604/170.03 |
| 4,964,850 A | | 10/1990 | Bouton et al. |
| 4,981,477 A | | 1/1991 | Schon et al. |
| 5,019,032 A | * | 5/1991 | Robertson ................... 128/898 |
| 5,139,502 A | | 8/1992 | Berg et al. |
| 5,139,510 A | | 8/1992 | Goldsmith, III et al. |
| 5,203,773 A | * | 4/1993 | Green ......................... 604/104 |
| 5,245,992 A | | 9/1993 | Nye |
| 5,246,455 A | | 9/1993 | Shikani |
| 5,279,610 A | | 1/1994 | Park et al. |
| 5,342,296 A | | 8/1994 | Persson et al. |
| 5,456,714 A | | 10/1995 | Owen |
| 5,470,320 A | | 11/1995 | Tiefenbrun et al. |
| 5,477,852 A | | 12/1995 | Landis et al. |
| 5,601,594 A | | 2/1997 | Best |
| 5,693,065 A | | 12/1997 | Rains, III |
| 5,897,521 A | | 4/1999 | Lavigne |
| 6,030,402 A | * | 2/2000 | Thompson et al. ......... 606/105 |

OTHER PUBLICATIONS

Shikani, The Shikani Middle Meatal Antrostomy Stent, unknown, unknown, unknown.

* cited by examiner

Primary Examiner—Glenn K. Dawson
Assistant Examiner—Michael G. Mendoza
(74) Attorney, Agent, or Firm—Bourque & Associates, P.A.

(57) ABSTRACT

A nasal intubation device is used to penetrate a nasal region and provide irrigation and/or medication to the nasal region. This intubation device can also be used in other applications. The intubation device comprises a flexible tube and a distal tip at the distal end of the flexible tube. The distal tip includes flanges forming a generally arrow shape that is capable of penetrating the nasal region and allowing the intubation device to remain within the nasal region. The flexible tube includes a passageway communicating with a perforated region proximate the distal end to provide the irrigation and/or medication. An implantation device, such as a canula-trocart, can be used to implant the intubation device.

12 Claims, 4 Drawing Sheets

NASAL INTUBATION DEVICE AND SYSTEM FOR INTUBATION

FIELD OF THE INVENTION

The present invention relates to tubes for medical applications and more particularly, to a nasal intubation device for penetrating and irrigating the ethmoid sinus region.

BACKGROUND OF THE INVENTION

Intubation devices, in general, are well known in the medical field. Tubes are often inserted into body passageways or cavities of a patient to ventilate, drain, and/or irrigate the cavity into which the tube in inserted. Continuing efforts are being made to design intubation devices that are easily and comfortably inserted into a patient, particularly when the tube must be left in place within the patient.

One medical use for an intubation device is in the treatment of chronic rhinosinusitis (CRS). CRS is a disease of the nasal and paranasal sinuses characterized by the symptoms of facial pain, nasal obstruction, and rhinorrhea. Dysfunction of the anterior ethmoidal cells is the main cause of chronic sinusitis. The ethmoid sinus is a complex labyrinth formed by independent cells. Under normal conditions, narrow spaces such as fissures and ostia are very resistant to infection. When corresponding mucosal areas are firmly pressed together, however, secretions cannot be eliminated by ciliary transport, providing ideal conditions for viral and bacterial growth.

When recurrent infection and clinical symptoms are not improved by medical therapy, surgery may be performed involving the removal of ethmoidal tissue and middle meatus antrostomy. The current surgical intervention that is recommended in these patients is functional endoscopic sinus surgery (FESS). This procedure is a drainage procedure that exteriorizes the ethmoid labyrinth into the superior nasal vault and opens the fronto nasal canal and maxillary ostium for drainage. This procedure removes the natural structure for the ethmoid to control the mucosal hypertrophy that is actually causing the persistence of symptoms.

However, some patients (e.g., 50% of allergic subjects) with diffuse disease do not benefit from the surgical procedures and exhibit persistent mucosal disease, which leads to repetitive antibiotic treatment and even surgical revisions. Surgical intervention, which increases exposure of the maxillary sinus mucosa to environmental air, may serve to increase mucosal inflammation and the need for surgical revision. Topical corticosteroid treatment has been used for reducing inflammation and ameliorating the symptoms of allergic rhinitis but has been less successful in patients with CRS. Intubation and irrigation of the maxillary cavity has been performed successfully, but existing intubation devices have been unable to effectively penetrate the ethmoidal sinus region to allow direct treatment of the ethmoidal sinus cells.

Accordingly, an intubation device and system is needed to treat chronic sinusitis or other similar conditions by penetrating the ethmoidal sinus region and by irrigation of the ethmoidal cells with medication without substantial disruption of the natural anatomy.

SUMMARY OF THE INVENTION

The present invention features a nasal intubation device comprising a flexible tube having a proximal end, a distal end, and a passageway extending from the proximal end to the distal end. A distal tip is located at the distal end of the flexible tube and includes a pointed end and flanges extending toward the proximal end of the flexible tube and at an angle with respect to the flexible tube. In one example, the flanges form an angle of about 30° with respect to the flexible tube. The flexible tube preferably includes a perforated area proximate the distal end, which communicates with the passageway. A support member, such as a ring, can be positioned around the distal end of the flexible and beneath the flanges. The width of the flanges preferably tapers outwardly away from the pointed end.

The present invention also features a nasal intubation system comprising an implantation device including a proximal end, a distal end, and a passageway extending from the proximal end to the distal end. The implantation device preferably has a bend proximate the distal end. The nasal intubation device is positioned within the passageway for insertion within the nasal passageway. The support member is capable of supporting the nasal intubation device on the distal end.

DESCRIPTION OF THE DRAWINGS

These and other features and advantages of the present invention will be better understood by reading the following detailed description, taken together with the drawings wherein.

DETAILED DESCRIPTION OF THE PREFERRED EMBODIMENT

Figure 1:
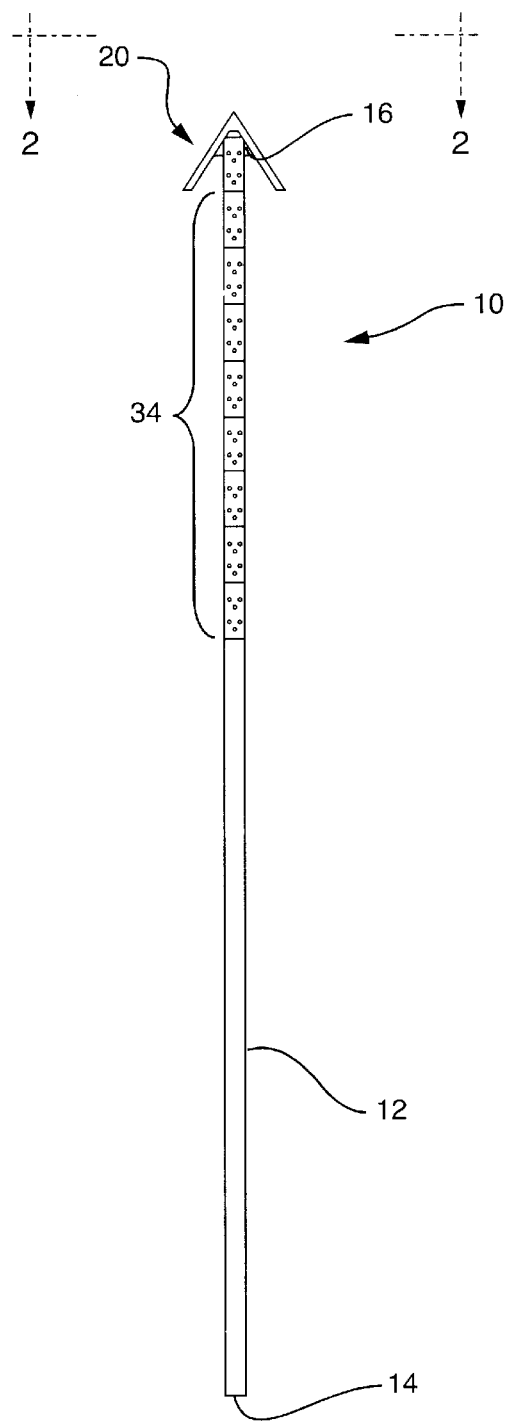
FIG. 1 is a side view of the nasal intubation device, according to the present invention.

The nasal intubation device 10, FIG. 1, according to the present invention, is capable of penetrating the ethmoid sinus and providing irrigation to the ethmoid cells, as will be described in greater detail below. Although the present invention is described in the context of this exemplary use, the nasal intubation device 10 can also be used in connection with other procedures in other passageways or cavities within the body.

The nasal intubation device 10 includes a flexible tube 12 having a proximal end 14 and a distal end 16. A distal tip 20 is located at the distal end 16 of the flexible tube 12. The distal tip 20 is preferably capable of penetrating into and anchoring the intubation device 10 within the ethmoidal sinus region or other desired location in a patient. In one embodiment, the distal tip 20 is indurated or hardened to allow the distal tip 20 to serve as a bore or punching tool to penetrate into the desired location. When the distal tip 20 is in place, the flexible tube 12 extends from the desired location within the patient to an access region within the patient. The flexible tube 12 and distal tip 20 are preferably made of themoplastic (TPI) or another suitable material.

Figure 2:
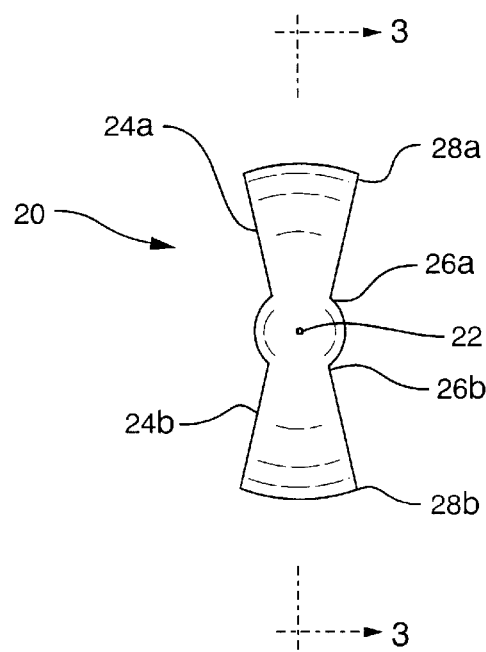
FIG. 2 is a top view of the nasal intubation device taken along line 2—2 in FIG. 1.

In one preferred embodiment, the distal tip 20, FIG. 2, is generally arrow shaped and includes a pointed end 22 and at least two flanges 24a, 24b. The width of each of the flanges 24a, 24b preferably tapers outwardly moving in a direction away from the pointed end 22 from a narrow portion 26a, 26b to a wide portion 28a, 28b of the respective flanges 24a, 24b. In one example, the narrow portion 26a, 26b of the respective flanges 24a, 24b, is about 1 mm, the wide portion 28a, 28b of the respective flanges 24a, 24b is about 2 mm, the distance from the pointed end 22 to the wide end 28a, 28b is about 6.5 mm, and the distance from the narrow end 26a, 26b to the wide end 28a, 28b of the respective flanges 24a, 24b is about 5 mm.

Figure 3:
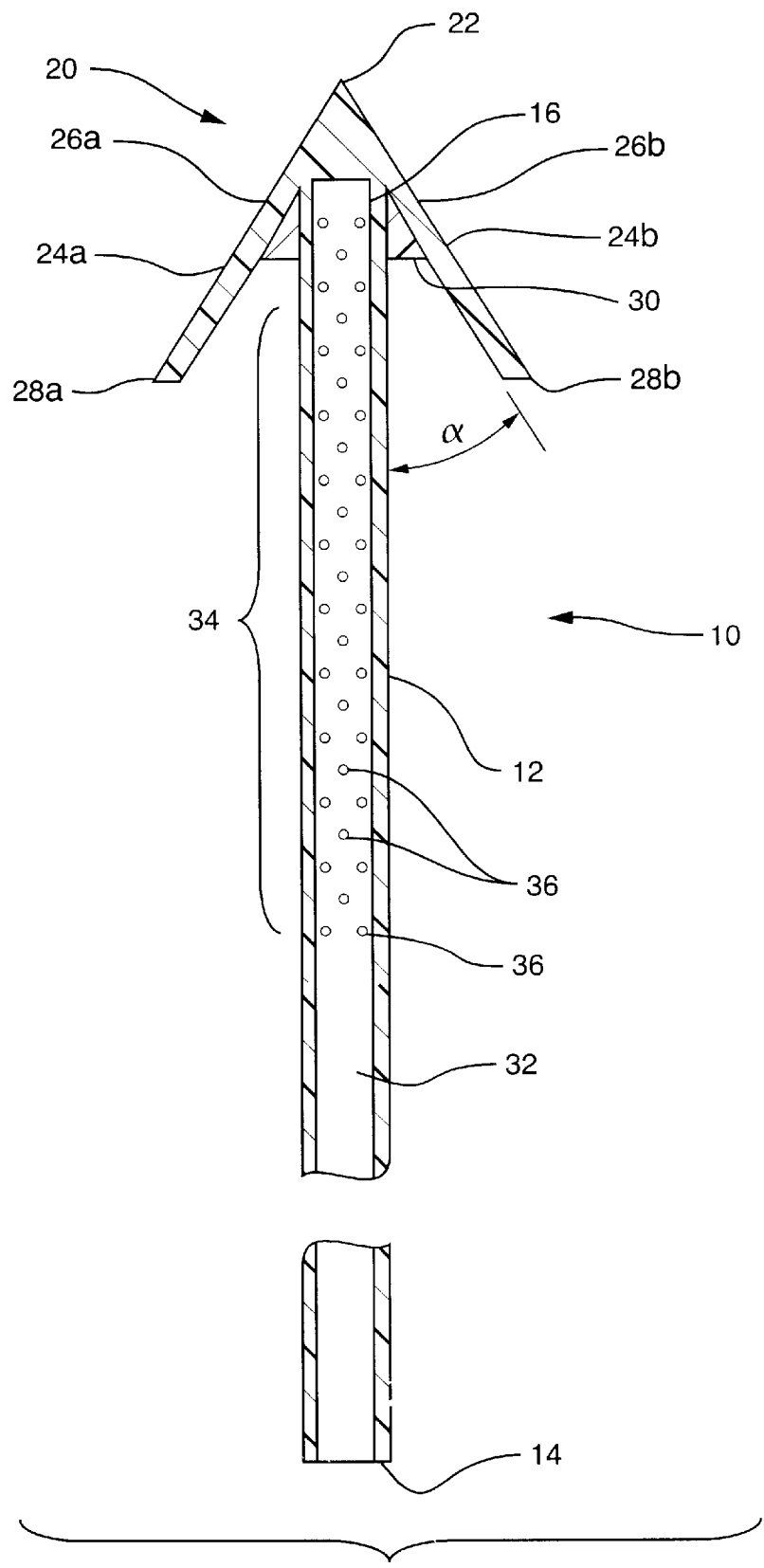
FIG. 3 is a cross-sectional view of the nasal intubation device taken along line 3—3 in FIG. 2.

The flanges 24a, 24b, FIG. 3, are preferably angled at an angle of α with respect to the flexible tube 12. In one example, the angle α is about 30°. In one preferred embodiment, a support member 30, such as a ring, is positioned beneath the flanges 24a, 24b to support the nasal intubation device 10 on a canula, as will be described in greater detail below. The support member 30 is preferably as hard as the tip 20 of the tube 12.

A passageway or canal 32 preferably extends from the proximal end 14 to the distal end 16 of the flexible tube 12. The flexible tube 12 preferably includes a perforated region 34 proximate the distal end 16. The perforated region 34 includes a plurality of holes 36 communicating with the passageway 32 for providing irrigation. In one example, the length of the flexible tube 12 from the proximal end 14 to the distal end 16 is about 100 mm, and the perforated region 34 can measure in the range of about 2–6 cm. The length of the perforated region 34 can be selected according to the extent of the area being treated, for example, the extent of the pathology of the ethmoid sinus.

Figure 4:
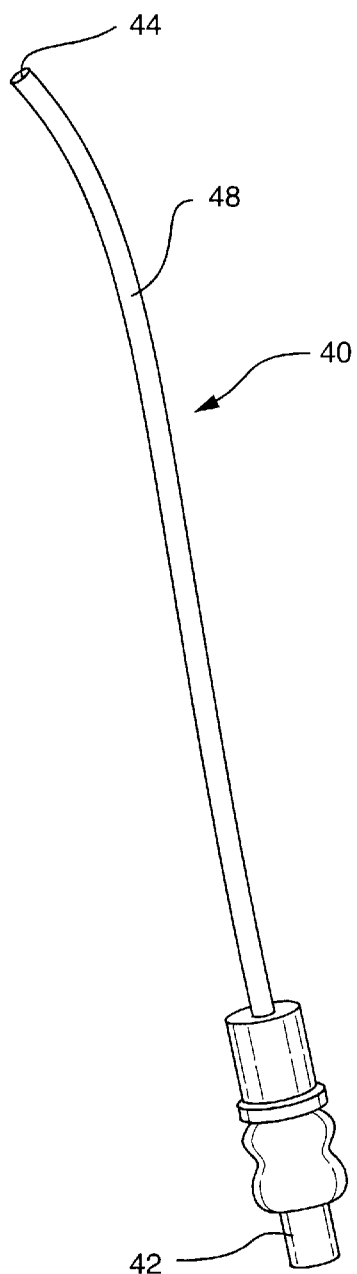
FIG. 4 is a side view of a canula used with the nasal intubation device, according to one embodiment of the present invention.

The nasal intubation device 10 is preferably used with an implantation device, such as a canula-trocart 40, FIG. 4. The canula-trocart 40 includes a canula proximal end 42, a canula distal end 44, and a passageway extending between the canula proximal end 42 and the canula distal end 44. The passageway of the canula-trocart 40 is preferably dimensioned to receive at least the flexible tube 12 of the intubation device 10. The length of the canula-trocart 40 is preferably sufficient to allow the canula-trocart 40 to reach the ethmoidal sinus region, and the canula-trocart 40 preferably includes a bend 48 proximate the canula distal end 44. According to one example, the external diameter of the canula-trocart 40 is about 2.2 mm, the internal diameter is about 1.8 mm, and the curved portion 48 extends for about 6 cm from the canula distal end 44. The canula proximal end 42 is preferably adapted to be coupled to an external device, for example, to provide suction or the delivery of medication through the canula-trocart 40.

Figure 5:
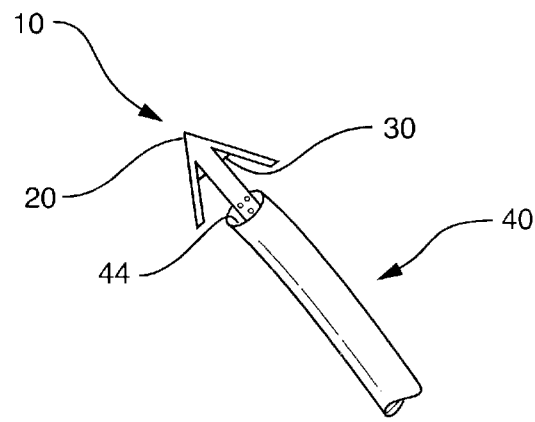
FIG. 5 is a side view of the end of the canula having the nasal intubation device extending therefrom, according to one embodiment of the present invention
Figure 6:
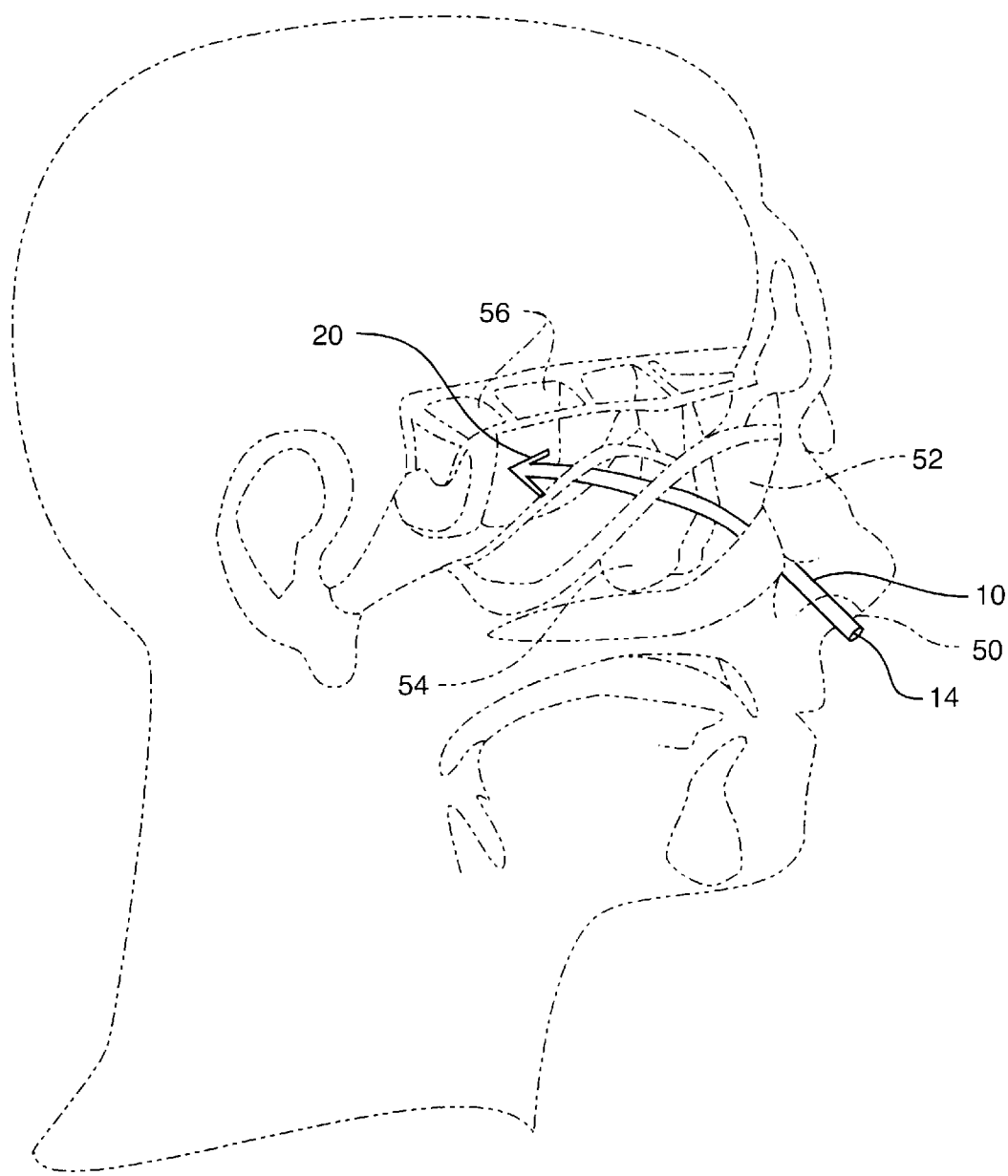
FIG. 6 is a schematic diagram of the nasal intubation device implanted within a patient, according to the present invention.

In use, the intubation device 10, FIG. 5, is inserted through the canula distal end 44 into the passageway within the canula-trocart 40 such that the distal tip 20 of the intubation device 10 extends beyond the canula distal tip 44. The support member 30 (FIG. 3) supports the distal tip 20 on the canula distal end 44 and allows the distal tip 20 to be used as a bore by transmitting pressure from the canula-trocart 40 to the distal tip 20. The canula-trocart 40 with the intubation device 10 in place is then passed through the nostril 50, FIG. 6, of a patient. According to one method, an endoscopic telescope can also be passed through the nostril at the same time to identify the anatomic landmarks of the middle turbinate, for example, the uncinate process 52 and the ethmoidal bulla 54.

The canula-trocart 40 pushes the distal tip 20 through the septum separating the ethmoidal cells, causing the distal tip 20 to penetrate the ethmoid sinus and successively puncture the anterior ethmoid cells 56. The curve 48 in the canula-trocart 40 prevents a penetration of the intra-cranial compartment and gives access successively to the ethmoidal cells 56. The canula-trocart 40 can also provide suction or the delivery of medication or irrigation, as needed. When the distal tip 20 of the intubation device is in the proper location within the ethmoidal cells 56, the canula-trocart 40 can be removed, releasing the intubation device 10. The flanges 24a, 24b of the distal tip 20 retain the intubation device 10 within the ethmoidal cells 56. When the intubation device 10 is left in place, the proximal end 14 is positioned generally at the nostril 50. Medication, such as topical corticosteroid, is injected through the proximal end 14 of the intubation device 10 and passes through the perforated area 34 of the intubation device 10 to directly treat the ethmoidal sinus cells 56. The anterior ethmoidal cells are particularly important because controlling inflammation in the anterior ethmoid area and the infundibulum frees the drainage of the frontal sinus and the maxillary sinus.

Accordingly, the intubation device of the present invention allows the ethmoidal cells to be treated directly by irrigation without disruption of the natural anatomy that protects the sinus from environmental contamination (e.g., allergens, virus and bacteria). The canula-trocart allows the intubation device to be implanted into the proper location and without substantially disrupting the natural anatomy.

Modifications and substitutions by one of ordinary skill in the art are considered to be within the scope of the present invention which is not to be limited except by the claims which follow.

What is claimed is:
1. A nasal intubation device comprising:
   a flexible tube having a proximal end, a distal end, and a passageway extending from said proximal end to said distal end; and
   a distal tip located at said distal end of said flexible tube, said distal tip including a pointed end and flanges extending toward said proximal end of said flexible tube and at an angle with respect to said flexible tube, said distal tip being made of a material sufficiently hard so as to be able to penetrate nasal bone and further including a support member disposed beneath said flanges for receiving pressure toward said distal tip during insertion.

2. The nasal intubation device of claim 1 wherein said flexible tube includes a perforated area proximate said distal end, and wherein said passageway communicates with said perforated area.

3. The nasal intubation device of claim 1 wherein said support member includes a ring disposed around said distal end.

4. The nasal intubation device of claim 1 wherein said flanges form an angle of about 30° with respect to said flexible tube.

5. The nasal intubation device of claim 1 wherein the width of said flanges tapers outwardly away from said pointed end.

6. A nasal intubation system comprising:
   a flexible tube having a tube proximal end, a tube distal end, and a tube passageway extending from said tube proximal end to said tube distal end; and
   a distal tip located at said tube distal end of said flexible tube, said distal tip being generally arrow-shaped and having at least two flanges, and further including a support member disposed beneath said flanges for supporting said distal tip on a distal end of an implantation device, said distal tip being made from a material sufficiently hard so as to be able to penetrate nasal bone; and said implantation device including a proximal end, said distal end, and a passageway extending from said proximal end to said distal end, wherein said flexible tube of said nasal intubation device is adapted to be positioned within said passageway of said implantation device such that said distal tip of said nasal intubation device and the support member are supported on said distal end of said implantation device.

7. The nasal intubation system of claim 6 wherein said flexible tube includes a perforated area proximate said tube distal end, and wherein said passageway communicates with said perforated area.

8. The nasal intubation system of claim 6 wherein said implantation device includes a bend proximate said distal end of said implantation device.

9. The nasal intubation system of claim 6 wherein said implantation device is a canula-trocart.

10. The nasal intubation system of claim 6 wherein said flanges form an angle of about 30° with respect to said flexible tube.

11. The nasal intubation system of claim 6 wherein the width of said flanges tapers outwardly away from said pointed end.

12. The nasal intubation system of claim 6 wherein said implantation device is adapted to provide at least one of suction and irrigation.

* * * * *